United States Patent
Nakano et al.

(10) Patent No.: US 11,945,643 B2
(45) Date of Patent: Apr. 2, 2024

(54) PRESSURE BAG

(71) Applicant: JMS CO., LTD., Hiroshima (JP)

(72) Inventors: Kiyomi Nakano, Hiroshima (JP); Megumi Uehara, Hiroshima (JP); Takahiko Kunishige, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 791 days.

(21) Appl. No.: 16/495,727

(22) PCT Filed: Mar. 28, 2018

(86) PCT No.: PCT/JP2018/012819
§ 371 (c)(1),
(2) Date: Sep. 19, 2019

(87) PCT Pub. No.: WO2018/181502
PCT Pub. Date: Oct. 4, 2018

(65) Prior Publication Data
US 2020/0095056 A1 Mar. 26, 2020

(30) Foreign Application Priority Data
Mar. 31, 2017 (JP) ................................ 2017-072087

(51) Int. Cl.
*B65D 75/00* (2006.01)
*A61J 1/10* (2006.01)
(Continued)

(52) U.S. Cl.
CPC ........... *B65D 83/62* (2013.01); *B65D 75/008* (2013.01); *B65D 83/0055* (2013.01); *A61J 1/10* (2013.01)

(58) Field of Classification Search
CPC .. B65D 83/62; B65D 75/008; B65D 83/0055; B65D 83/005
(Continued)

(56) References Cited

U.S. PATENT DOCUMENTS 5,013,303 A * 5/1991 Tamari ................ A61M 5/1483
604/131
5,505,708 A * 4/1996 Atkinson ............ A61M 5/1486
604/410

(Continued)

FOREIGN PATENT DOCUMENTS

CN 102076480 5/2011
CN 102510830 6/2012
(Continued)

OTHER PUBLICATIONS

Second Office Action issued in corresponding Chinese Patent Application No. 201880020585.X, dated Jul. 20, 2022, 12 pages w/translation.

*Primary Examiner* — Anthony D Stashick
*Assistant Examiner* — L Kmet
(74) *Attorney, Agent, or Firm* — HSML, P.C.

(57) ABSTRACT

A pressure bag (1) has a bag-like shape including an opening (11) at one end thereof and a bottom portion (12) on the opposite side to the opening (11). The pressure bag (1) has a double structure in which an inner sheet (20) and an outer sheet (30) are laid one on top of the other so that the outer sheet (30) is located on the opposite side of the inner sheet (20) from the housing chamber (10). A pressure chamber (15) is provided between the inner sheet (20) and the outer sheet (30). All of the inner sheet (20), the outer sheet (30), and the pressure chamber (15) extend from one side to the other side of the housing chamber (10) via the bottom portion (12).

6 Claims, 14 Drawing Sheets

(51) Int. Cl.
 *B65D 83/00* (2006.01)
 *B65D 83/62* (2006.01)
(58) Field of Classification Search
 USPC .......................................................... 206/438
 See application file for complete search history.

(56) References Cited

U.S. PATENT DOCUMENTS

| | | |
|---|---|---|
| 6,056,724 A | 5/2000 | Lacroix |
| 2011/0259510 A1 | 10/2011 | Foucaut et al. |
| 2012/0217180 A1 | 8/2012 | Kurose et al. |
| 2013/0066294 A1 | 3/2013 | Wake |
| 2016/0235627 A1 | 8/2016 | Morimoto et al. |

FOREIGN PATENT DOCUMENTS

| | | |
|---|---|---|
| CN | 102989028 | 3/2013 |
| CN | 105722492 | 6/2016 |
| CN | 106364738 | 2/2017 |
| JP | 2007-029562 | 2/2007 |
| JP | 2011-019709 | 2/2011 |

\* cited by examiner

PRESSURE BAG

TECHNICAL FIELD

The present invention relates to a pressure bag for applying pressure to a bag-shaped container in which a liquid substance is contained, and more particularly relates to a pressure bag that is used to apply pressure to the bag-shaped container and thereby squeeze the liquid substance out of the bag-shaped container.

BACKGROUND ART

Enteral nutrition therapy is known as a method for administering a liquid substance including a nutritional agent, a liquid diet, medicine, or the like to a patient where there are difficulties in feeding food from the oral cavity into the stomach as a result of an injury, a disease, a surgical operation, or the like of the esophagus or the oral cavity. In enteral nutrition therapy, a liquid substance that is contained in a bag-shaped container (also called "pouch", "laminate pack", or the like) formed by bonding flexible sheets to each other is fed into the body of a patient via a pliable catheter (commonly called "enteral nutrition catheter"). A nasal catheter that is inserted from the nasal cavity into the stomach or the duodenum of a patient, a PEG (Percutaneous Endoscopic Gastrostomy) catheter that is inserted into the stomach of a patient through a gastric fistula formed in the abdomen of the patient, and the like are known as catheters for use in enteral nutrition therapy.

If the liquid substance administered to the patient has low viscosity, problems may arise, such as reflux of the liquid substance in the stomach to the esophagus occurring and causing pneumonia as a complication, or water in the liquid substance not being completely absorbed by the body and causing diarrhea. To prevent these problems, the liquid substance is often thickened to a high viscosity.

However, when a liquid substance is thickened to a high viscosity, the fluidity thereof decreases. In order to feed a liquid substance that is thickened to a high viscosity into the body of a patient, it is necessary to compress a bag-shaped container in which the liquid substance is contained. When attempting to perform this operation with bare hands, an extremely large force is required, and therefore, a considerable burden is imposed on a worker (e.g., a nurse or a caregiver).

To address this issue, a squeezing device that is configured to be able to apply pressure to a bag-shaped container and squeeze a liquid substance out of the bag-shaped container has been proposed (e.g., see Patent Documents 1 and 2). A squeezing device includes a pressure bag that inflates when injected with air. In a squeezing device disclosed in Patent Document 1, a single pressure bag is disposed on one side of the bag-shaped container. In a squeezing device disclosed in Patent Document 2, two pressure bags are disposed on both sides of the bag-shaped container. In both of the squeezing devices, when a pressure bag is inflated, the pressure bag applies pressure to the bag-shaped container adjacent thereto, causing the liquid substance to be squeezed out of the bag-shaped container.

CITATION LIST

Patent Documents

Patent Document 1: JP 2007-029562A
Patent Document 2: JP 2011-019709A

DISCLOSURE OF INVENTION

Problem to be Solved by the Invention

However, both of the above-described squeezing devices have a problem in that it is difficult to squeeze all of the liquid substance in the bag-shaped container out of the bag-shaped container. In general, a bag-shaped container has a substantially rectangular shape in a plan view, and a port (also called "spout") through which the liquid substance flows out is provided on the side of one of the short sides thereof. If a conventional squeezing device is used, the liquid substance is likely to remain near the short side that is opposite to the short side on which the port is provided.

Moreover, the structure and the production process of the squeezing device disclosed in Patent Document 2 are complicated because of the need to connect the two independent pressure bags to each other so that a bag-shaped container can be housed therebetween.

An object of the present invention is to provide a pressure bag with which the amount of liquid substance remaining in a bag-shaped container after being squeezed out of the bag-shaped container is reduced, and which has a simple structure and can be produced with ease.

Means For Solving Problem

A pressure bag of the present invention includes a housing chamber for housing a bag-shaped container in which a liquid substance is contained and a hermetically-sealed pressure chamber, and is configured such that when a fluid is injected into the pressure chamber, the pressure chamber is inflated and applies pressure to the bag-shaped container housed in the housing chamber, and thus can squeeze the liquid substance out of the bag-shaped container. The pressure bag has a bag-like shape including, at one end thereof, an opening through which the bag-shaped container is placed into and taken out of the housing chamber, and also including a bottom portion on the opposite side to the opening. The pressure bag has a double structure in which a flexible inner sheet and a flexible outer sheet are laid one on top of another so that the outer sheet is located on the opposite side of the inner sheet from the housing chamber. The pressure chamber is provided between the inner sheet and the outer sheet. All of the inner sheet, the outer sheet, and the pressure chamber between the inner sheet and the outer sheet extend from one side to another side of the housing chamber via the bottom portion.

Effects of the Invention

According to the present invention, the amount of liquid substance remaining in a bag-shaped container after being squeezed out of the bag-shaped container can be reduced. Also, the pressure bag of the present invention has a simple structure and can be produced with ease.

DESCRIPTION OF THE INVENTION

Figure 1:
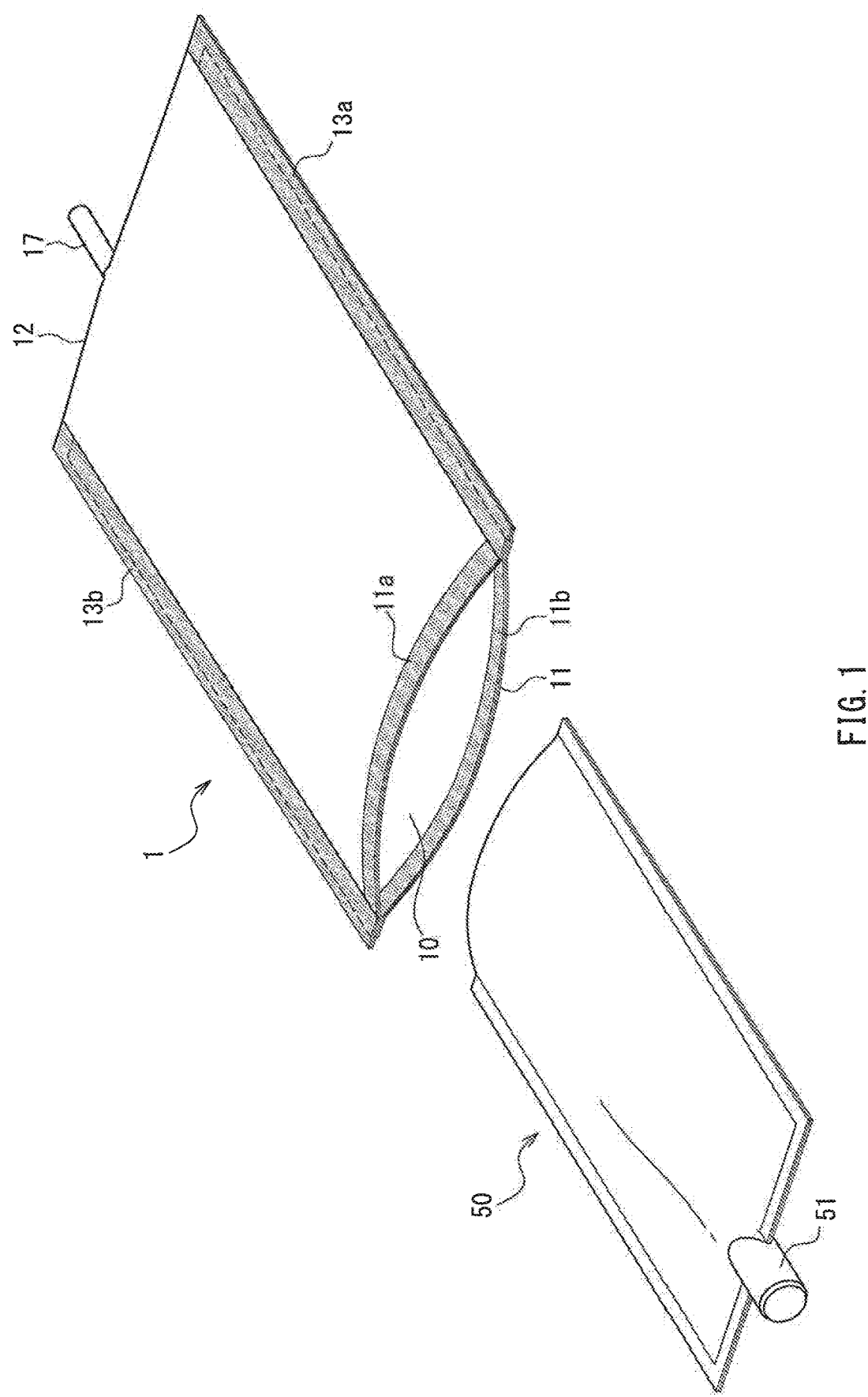
FIG. 1 is a perspective view showing a pressure bag according to Embodiment 1 of the present invention and a bag-shaped container to be housed in the pressure bag.

In the above-described pressure bag of the present invention, either of or both the inner sheet and the outer sheet may be composed of a single continuous sheet. This configuration is advantageous in simplifying the structure of the pressure bag and facilitating the production thereof.

The inner sheet may be folded back at a folding-back portion. In this case, the folding-back portion of the inner sheet may be disposed on the bottom portion side. With this configuration, the inner sheet can be composed of a single continuous sheet. Accordingly, this configuration is advantageous in simplifying the structure of the pressure bag and facilitating the production thereof.

Similarly, the outer sheet may be folded back at a folding-back portion. In this case, the folding-back portion of the outer sheet may be disposed on the bottom portion side. With this configuration, the outer sheet can be composed of a single continuous sheet. Accordingly, this configuration is advantageous in simplifying the structure of the pressure bag and facilitating the production thereof.

In the present invention, "folding back" a sheet means that a sheet having a first surface and a second surface that constitute a front side and a back side thereof is folded back such that portions of the first surface oppose each other. The "folding-back portion" means a leading end portion at which the sheet is folded back. In the "folding-back portion", the sheet is folded along one or more folds (also referred to as fold lines). That is to say, in the present invention, the wording "a sheet is folded back" includes not only a case where the sheet is folded back at a single fold into a substantially "V" shape or a substantially "U" shape (i.e., the sheet is simply folded in half), but also a case where the sheet is folded at a plurality of folds in the folding-back portion (e.g., the sheet is alternately mountain-folded and valley-folded into a substantially "M" shape or the like) but is regarded as being folded back when viewed as a whole.

Outer peripheral end edges of the inner sheet may be entirely joined to the outer sheet. With this configuration, it is possible to obtain a hermetically-sealed pressure chamber with a simple configuration.

At the bottom portion, the inner sheet and the outer sheet may be spaced apart from each other in a direction in which the opening and the bottom portion are connected to each other. This configuration is advantageous in allowing portions of the pressure chamber that are located on opposite sides of the housing chamber to be in communication with each other via the bottom portion.

At the bottom portion, the inner sheet and the outer sheet need not be joined to each other. This configuration is advantageous in allowing the portions of the pressure chamber that are located on opposite sides of the housing chamber to be in communication with each other via the bottom portion. Moreover, this configuration is advantageous in simplifying the structure of the pressure bag and facilitating the production thereof.

The inner sheet may constitute an inner surface of the housing chamber, and the outer sheet may constitute an outer surface of the pressure bag. This configuration is advantageous in simplifying the structure of the pressure bag and facilitating the production thereof.

The pressure bag of the present invention may further include a communicating tube through which the fluid is injected into the pressure chamber. With this configuration, the fluid can flow into and out of the pressure chamber via the communicating tube.

Hereinafter, the present invention will be described in detail while presenting preferred embodiments thereof. However, it goes without saying that the present invention is not limited to the embodiments below. In the drawings that will be referred to in the following description, the embodiments of the present invention are shown in a simplified manner. Accordingly, portions shown in the drawings below may be changed or omitted, or optional members or configurations that are not shown in the drawings below may be added, within the scope of the present invention. In the drawings that will be referred to in the description of the embodiments below, members corresponding to those members shown in a drawing that is referred to in the description of any preceding embodiment are denoted by the same reference numerals as the members shown in the drawing of that preceding embodiment. With respect to such members, redundant descriptions are omitted, and the description of the preceding embodiment should be taken into account as appropriate. Moreover, it should be understood that the dimensional ratios of portions in the drawings below are not necessarily the same as the actual dimensional ratios of those portions.

Embodiment 1

FIG. 1 is a perspective view showing a pressure bag 1 according to Embodiment 1 of the present invention and a bag-shaped container 50 in which a liquid substance is contained. The pressure bag 1 has a bag-like shape that has a substantially rectangular shape in a plan view. The pressure bag 1 includes a housing chamber 10 for housing the bag-shaped container 50. An opening 11, which is the sole opening, through which the bag-shaped container 50 is placed into and taken out of the housing chamber 10 is provided at one end (one short side in Embodiment 1) of the substantially rectangular shape in a plan view. The housing chamber 10 is in communication with the outside only via the opening 11. A bottom portion 12 of the bag-like shape is located on the opposite side (the other short side in Embodiment 1) to the opening 11. Opening seal portions 11a and 11b are provided along end edges of the opening 11. Lateral side seal portions 13a and 13b are provided along a pair of lateral sides (i.e., the pair of long sides of the substantially rectangular shape) that connect the opening 11 and the bottom portion 12 to each other. In FIG. 1, the opening seal portions 11a and 11b as well as the lateral side seal portions 13a and 13b are shaded with numerous dots. A communicating tube 17 is provided in the bottom portion 12. For the sake of convenience of the following description, a direction in which the opening 11 and the bottom portion 12 are connected to each other (i.e., direction in which the bag-shaped container 50 is placed into and taken out of the housing chamber 10 via the opening 11, and which coincides with the long-side direction of the pressure bag 1 in Embodiment 1) will be referred to as "insertion and withdrawal direction".

Figure 2:
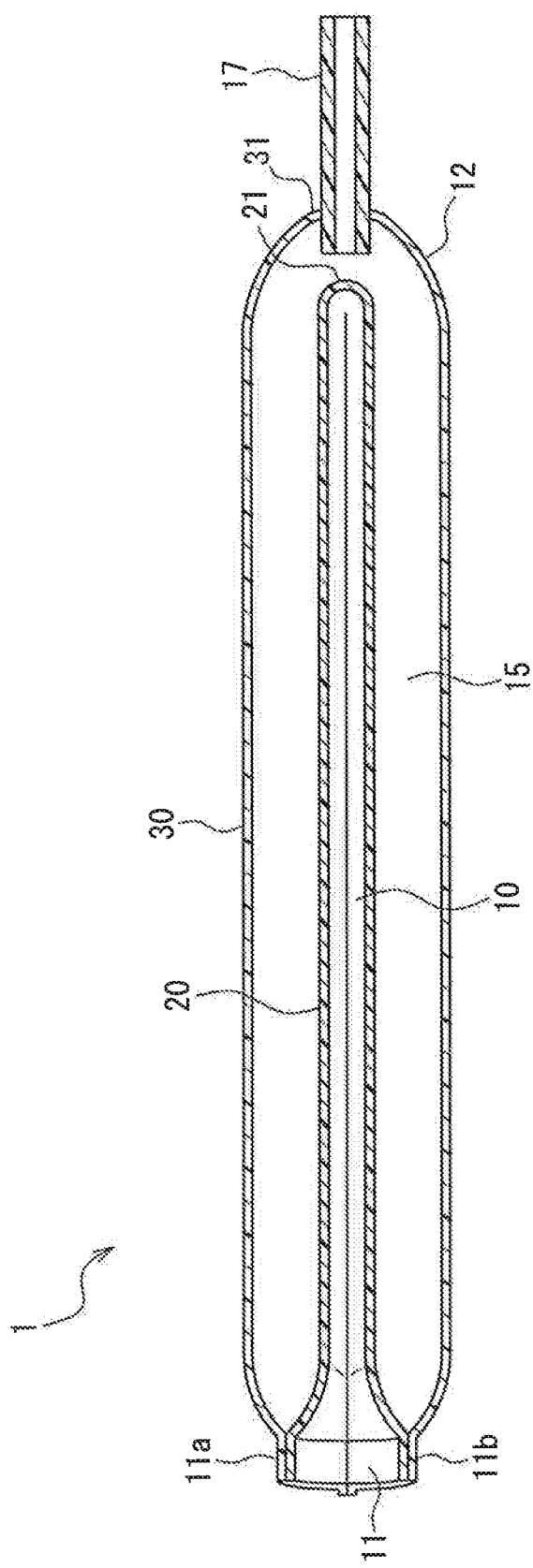
FIG. 2 is a cross-sectional view of the pressure bag according to Embodiment 1 of the present invention.

FIG. 2 is a cross-sectional view of the pressure bag 1 taken along a plane that is parallel to the insertion and withdrawal direction. The pressure bag 1 includes a single inner sheet 20 that is folded back at a folding-back portion 21, and a single outer sheet 30 that is folded back at a folding-back portion 31. The inner sheet 20 constitutes an inner surface of the housing chamber 10, and the outer sheet 30 constitutes an outer surface of the pressure bag 1. The pressure bag 1 has a double structure in which the inner sheet 20 and the outer sheet 30 that is located on the opposite side (outer side) of the inner sheet 20 from the housing chamber 10 are laid one on top of the other. The folding-back portion 21 of the inner sheet 20 and the folding-back portion 31 of the outer sheet 30 are disposed on the bottom portion 12 side of the pressure bag 1. The folding-back portion 21 of the inner sheet 20 and the folding-back portion 31 of the outer sheet 30 are spaced apart from each other in the insertion and withdrawal direction (left-right direction in FIG. 2), rather than being in contact with each other.

On one side (upper side in FIG. 2) of the housing chamber 10, the inner sheet 20 and the outer sheet 30 are sealed together at the opening seal portion 11a, and on the other side (lower side in FIG. 2) of the housing chamber 10, the inner sheet 20 and the outer sheet 30 are sealed together at the opening seal portion 11b. Also, at each of the lateral side seal portions 13a and 13b (see FIG. 1), portions of the inner sheet 20 that face each other and portions of the outer sheet 30 that are located laterally outward of those portions of the inner sheet 20 are sealed together. As a result, the hermetically-sealed pressure chamber 15 is formed between the inner sheet 20 and the outer sheet 30. All of the inner sheet 20, the outer sheet 30, and the pressure chamber 15 between the inner sheet 20 and the outer sheet 30 extend in a substantially "U" shape (or substantially "V" shape) from one side (upper side in FIG. 2) to the other side (lower side in FIG. 2) of the housing chamber 10 via the bottom portion 12. The inner sheet 20 and the outer sheet 30 are not sealed together at the bottom portion 12 (except for the lateral side seal portions 13a and 13b). For this reason, it is ensured that portions of the pressure chamber 15 that are located on opposite sides of the housing chamber 10 are in communication with each other via the bottom portion 12.

The communicating tube 17 has a hollow cylindrical shape and penetrates the outer sheet 30 at a position in the folding-back portion 31 of the outer sheet 30. The pressure chamber 15 is in communication with the outside via the communicating tube 17.

In FIG. 2, in order to facilitate understanding of the configuration of the pressure bag 1, portions of the inner sheet 20 that oppose each other via the housing chamber 10 are slightly spaced apart from each other, and the inner sheet 20 and the outer sheet 30 that oppose each other via the pressure chamber 15 are slightly spaced apart from each other. However, in an actual pressure bag 1 when not in use, the portions of the inner sheet 20 that oppose each other via the housing chamber 10 may be in close contact with each other, and the inner sheet 20 and the outer sheet 30 that oppose each other via the pressure chamber 15 may be in close contact with each other. That is to say, the pressure bag 1 when not in use may have a thin plate-like shape in which two layers of the outer sheet 30 and two layers of the inner sheet 20 between the two layers of the outer sheet 30 are in close contact with one another.

The inner sheet 20 and the outer sheet 30 have flexibility (or pliability) so that they can be easily deformed. Preferably, the inner sheet 20 and the outer sheet 30 also have sealability so that even when a fluid (e.g., air) is injected into the pressure chamber 15 under a predetermined pressure (e.g., 60 kPa), the fluid is prevented from leaking to the outside, and mechanical strength so that even when the fluid is injected as described above, the pressure bag 1 is prevented from exploding. As long as these properties are satisfied, there is no limitation on the materials of the inner sheet 20 and the outer sheet 30, and, for example, resin materials, such as polyethylene terephthalate, nylon, polypropylene, polyethylene, and soft polyvinyl chloride, can be used. The inner sheet 20 and the outer sheet 30 may each be a laminated sheet in which a plurality of layers made of different materials are laminated. The materials of the inner sheet 20 and the outer sheet 30 may be the same or may be different. In order for pressure to be effectively applied to the bag-shaped container 50 in the housing chamber 10 when the pressure chamber 15 is inflated, it is preferable that the outer sheet 30 has substantially no stretchability. The inner sheet 20 may or may not have stretchability.

Any material can be used for the communicating tube 17 as long as the pressure chamber 15 can be in communication with the outside via the communication tube 17. Both a substantially undeformable hard material and an easily deformable soft material may be used. Examples of the hard material that can be used include resin materials, such as polyethylene, polypropylene, polyacetal, polycarbonate, polyethylene terephthalate, polybutylene terephthalate, butylene-styrene block copolymers, polyoxymethylene, acrylonitrile-butadiene-styrene copolymers, polystyrene, polyamide, and hard polyvinyl chloride; as well as metal materials, such as stainless steel, iron, and aluminum. Examples of the soft material that can be used include rubber, such as natural rubber, isoprene rubber, and silicone rubber; thermoplastic elastomers, such as styrene elastomers, olefin elastomers, and polyurethane elastomers; and soft polyvinyl chloride.

The pressure chamber 15 of the pressure bag 1 is inflated as a result of a fluid being injected into the pressure chamber 15 via the communicating tube 17. The fluid to be injected may be either a gas or a liquid, but a gas, in particular, air is preferable. Although not shown in FIGS. 1 and 2, when the pressure bag 1 is in use, a pump for injecting the fluid into the pressure chamber 15 is connected to the communicating tube 17 via a pliable tube. In the case where air is used as the fluid, a manual piston pump or a manual air balloon can be used as the pump. The piston pump discharges air when a piston is inserted into and withdrawn from a cylinder. The air balloon is a hollow body made of rubber or the like and has a spherical shape, a rugby ball shape, or the like, and discharges air when compressed. However, the pump is not limited to these, and may also be a manual pump other than a piston pump and an air balloon, or any electric pump. A pressure indicator that indicates the pressure in the pressure chamber 15, a pressure release valve (e.g., three-way stopcock) for releasing the fluid to the outside and thereby reducing the pressure in the pressure chamber 15, and the like may be provided on the tube that connects the communicating tube 17 and the pump to each other.

The pressure bag 1 is used to apply pressure to and squeeze out the liquid substance that is contained in the bag-shaped container 50 (see FIG. 1). The bag-shaped container 50 is preferably, but is not limited to, for example, a bag-shaped product that is composed of a flexible sheet and commonly called a "pouch" or "laminate pack". In Embodiment 1, the bag-shaped container 50 is a standing pouch composed of two substantially rectangular sheets constituting two side surfaces thereof and a single sheet constituting a bottom surface thereof (in FIG. 1, only the sheet constituting one side surface can be seen). However, the bag-shaped container 50 is not limited to this, and may have any configuration, such as a flat bag-type pouch in which two sheets having the same dimensions are laid one on top of the other and bonded to each other at outer peripheral end edges thereof, and a box-shaped pouch (also referred to as "square bottom pouch") in which gussets are provided in lateral side surfaces and a bottom surface. The bag-shaped container 50 is provided with a port (also called "spout") 51 through which the liquid substance flows out. In Embodiment 1, the port 51 is provided in the middle of a short side of the bag-shaped container 50, which has a substantially rectangular shape in a plan view. However, the position of the port 51 is not limited to this position, and, for example, the port 51 may be provided in a corner portion where a short side and a long side intersect each other, while being inclined relative to the short side and the long side.

There is no limitation on the type of liquid substance contained in the bag-shaped container 50. For example, the liquid substance may be any liquid substance, such as a nutritional agent (e.g., enteral nutritional agent used in enteral nutrition therapy), a liquid diet, a contrast medium, hyaluronic acid, a physiological saline solution, and blood. The liquid substance may be thickened (or semi-solid) to a high viscosity of 1,000 mPa·s or more, for example. Preferably, the upper limit of the viscosity of the liquid substance is, but is not limited to, 50,000 mPa·s or less.

Next, an example of a method for producing the pressure bag 1 will be described.

Figure 3A:
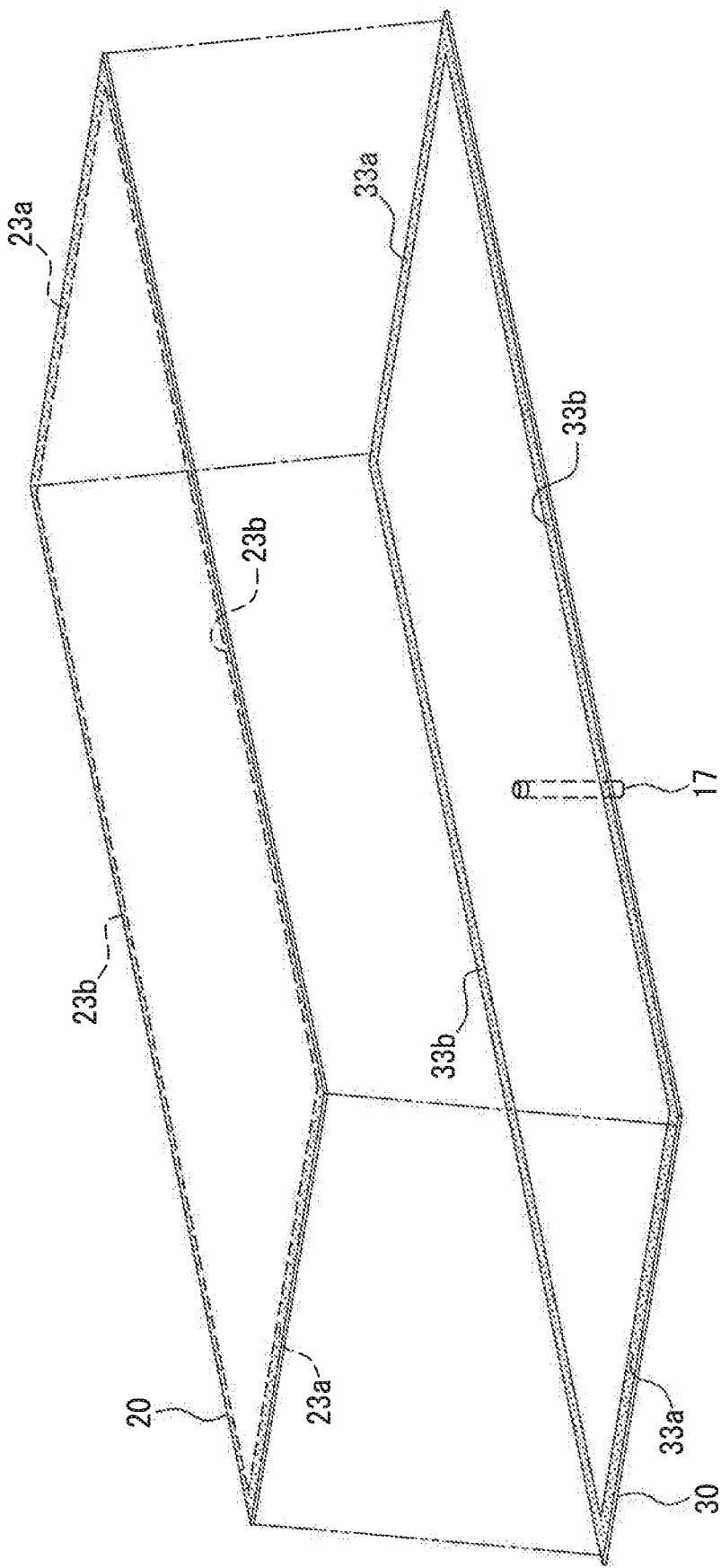
FIG. 3A is a perspective view illustrating a step of a method for producing the pressure bag according to Embodiment 1 of the present invention.

First, as illustrated in FIG. 3A, the inner sheet 20 and the outer sheet 30 are prepared. Both the inner sheet 20 and the outer sheet 30 have an elongated rectangular shape. The outer sheet 30 is larger than the inner sheet 20 both in the long-side direction and in a short-side direction of the rectangular shapes thereof.

The communicating tube 17 is provided penetrating the outer sheet 30 in or near the middle (position of the intersection of the two diagonal lines) of the outer sheet 30. An outer circumferential surface of the communicating tube 17 and the outer sheet 30 are joined to each other in an airtight manner. There is no limitation on the method for joining the communicating tube 17 and the outer sheet 30 to each other, but, for example, a method in which an adhesive is applied, a fusion-bonding method, or the like can be used.

On a surface (lower surface of the inner sheet 20 in FIG. 3A) of the inner sheet 20 that is located on the side opposing the outer sheet 30, sealant regions 23*a* and 23*b* to which a known heat sealant is applied are continuously provided along the outer peripheral end edges of the inner sheet 20. Similarly, on a surface (upper surface of the outer sheet 30 in FIG. 3A) of the outer sheet 30 that is located on the side opposing the inner sheet 20, sealant regions 33*a* and 33*b* to which a known heat sealant is applied are continuously provided along the outer peripheral end edges of the outer sheet 30. The sealant regions 23*a* and 33*a* extend along the short sides of the sheets 20 and 30, and the sealant regions 23*b* and 33*b* extend along the long sides of the sheets 20 and 30. The sealant regions 23*a* and the sealant regions 33*a* have substantially the same width. The sealant regions 33*b* are slightly wider than the sealant regions 23*b*. In FIG. 3A, the sealant regions 23*a*, 23*b*, 33*a*, and 33*b* are shaded with numerous dots.

Figure 3B:
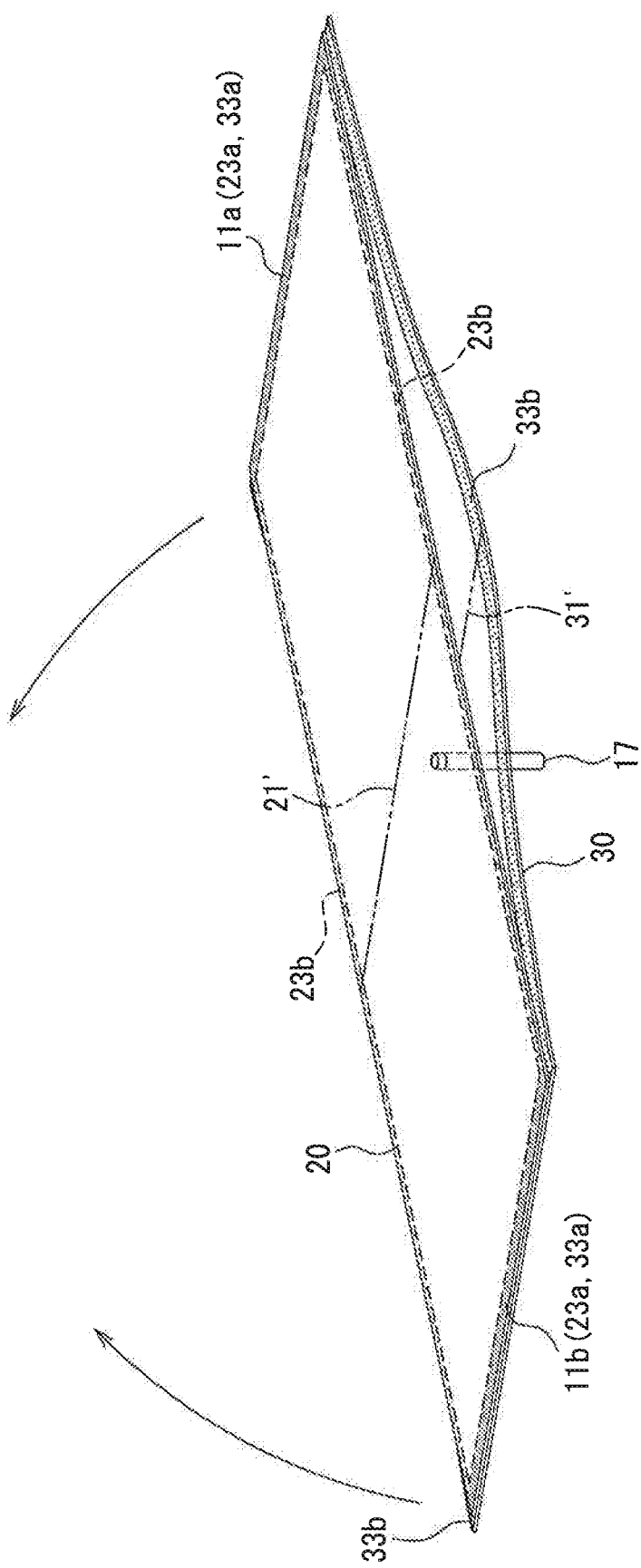
FIG. 3B is a perspective view illustrating the next step of the method for producing the pressure bag according to Embodiment 1 of the present invention.

Next, as illustrated in FIG. 3B, the pair of short sides of the inner sheet 20 are laid on top of the pair of short sides of the outer sheet 30. Then, the sealant regions 23*a* of the inner sheet 20 are joined to the respective sealant regions 33*a* of the outer sheet 30 through heat sealing. The thus heat-sealed regions constitute the opening seal portions 11*a* and 11*b* (see FIGS. 1 and 2). Since the outer sheet 30 is longer than the inner sheet 20 in the long-side direction, even when the inner sheet 20 is straightened in the long-side direction, a middle portion of the outer sheet 30 has slack. Moreover, since the outer sheet 30 is longer than the inner sheet 20 in the short-side direction, a portion of each sealant region 33*b* of the outer sheet 30 extending along a long side thereof protrudes outward in the short-side direction from the inner sheet 20.

Figure 3C:
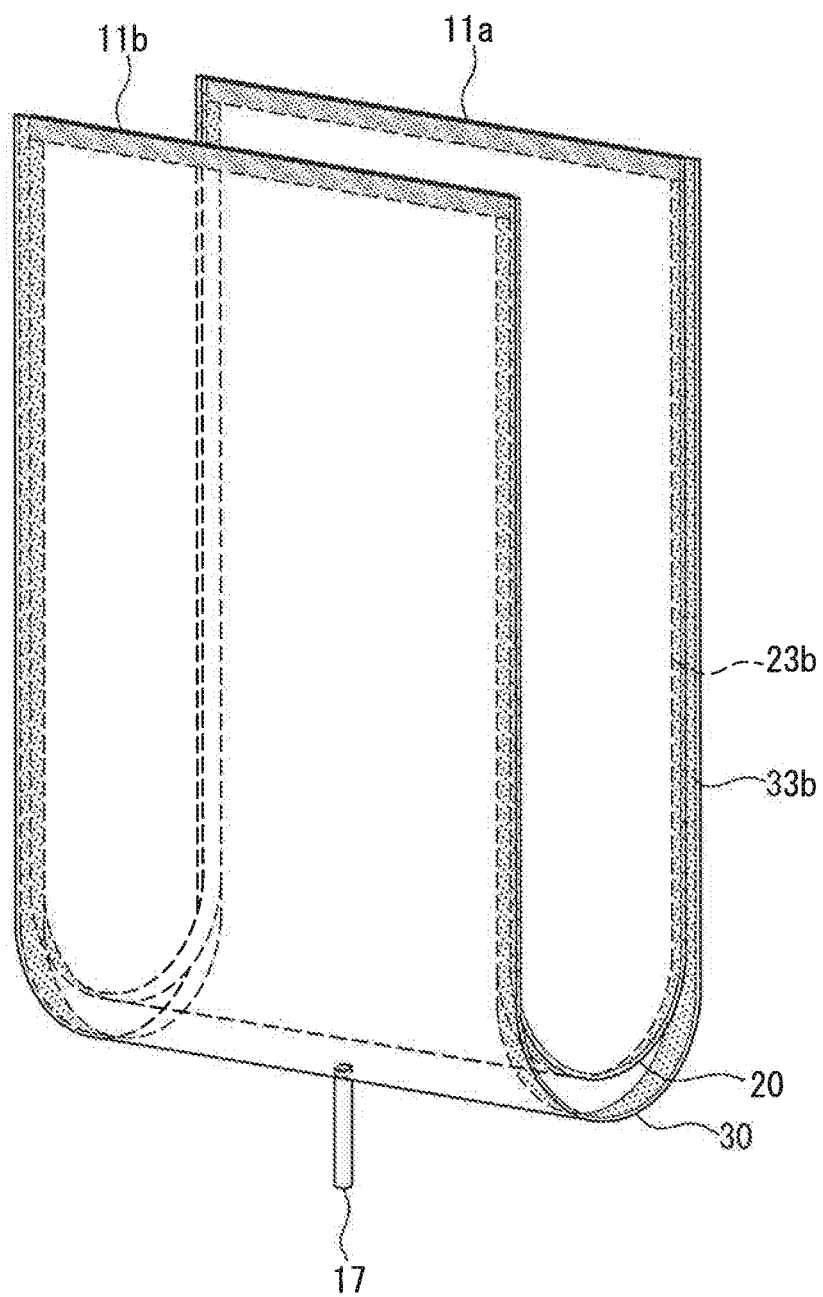
FIG. 3C is a perspective view illustrating the further next step of the method for producing the pressure bag according to Embodiment 1 of the present invention.

Next, as illustrated in FIG. 3C, the inner sheet 20 and the outer sheet 30 are folded back (i.e., folded in half) with the inner sheet 20 located on the inner side so that the opening seal region 11*a* and the opening seal region 11*b*, which extend along the short sides, are laid one on top of the other. Line-double dash lines 21' and 31' in FIG. 3B indicate the folds of the sheets 20 and 30. The folds 21' and 31' constitute the folding-back portions 21 and 31 (see FIG. 2) of the pressure bag 1. The sealant regions 23*b* of the inner sheet 20 face the respective sealant regions 33*b* of the outer sheet 30. The portions of the sealant regions 33*b* of the outer sheet 30 that protrude from the inner sheet 20 face themselves as a result of the outer sheet 30 being folded back. In the state in which the sheets 20 and 30 are folded back, the sealant regions 23*b* and 33*b* are joined together through heat sealing. The thus heat-sealed regions constitute the lateral side seal portions 13*a* and 13*b* (see FIG. 1). In the lateral side seal portions 13*a* and 13*b*, the long sides of the inner sheet 20 are joined to the outer sheet 30, and the long sides of the outer sheet 30 are joined to themselves after being folded back. Thus, the pressure bag 1 shown in FIGS. 1 and 2, which has a bag-like shape with the opening 11 provided at one end thereof, is obtained. As can be readily understood from the above-described production method, the outer peripheral end edges, where the sealant regions 23*a* are 23*b* are provided, of the inner sheet 20 are entirely joined to the outer sheet 30. Therefore, the hermetically-sealed pressure chamber 15 is formed between the inner sheet 20 and the outer sheet 30. The pressure chamber 15 is in communication with the outside only via the communicating tube 17. The pressure chamber 15 is folded back at the bottom portion 12.

Next, a method for using the pressure bag 1 will be described taking, as an example, a case where enteral nutrition therapy is performed by inflating the pressure chamber 15 using air and thereby squeezing a liquid substance (enteral nutritional agent) contained in the bag-shaped container 50 out of the bag-shaped container 50.

As shown in FIG. 1, the pressure bag 1 and the bag-shaped container 50 are prepared. The pressure chamber 15 (see FIG. 2) of the pressure bag 1 is not substantially inflated, and the inner sheet 20 and the outer sheet 30 that define the pressure chamber 15 are substantially in close contact with each other. A pump (e.g., manual piston pump) is connected to the communicating tube 17 via a pliable tube (both are not shown, see FIGS. 8 and 9, which will be described later). An enteral nutritional agent is contained in the bag-shaped container 50. The port 51 of the bag-shaped container 50 and a PEG catheter inserted into a gastro fistula of a patient are connected to each other via a pliable extension tube (e.g., enteral nutrition set, which is not shown). The extension tube is provided with a clamp (not shown) for opening and closing a flow path in the extension tube. The flow path in the extension tube is closed by using the clamp.

The bag-shaped container 50 is placed into the housing chamber 10 from the opening 11 of the pressure bag 1, with the bottom portion (portion on the opposite side to the port 51) of the bag-shaped container 50 directed toward the pressure bag 1. The internal dimensions of the housing chamber 10 are set to be such dimensions that enable almost the entire bag-shaped container 50 to be housed therein. The extension tube (not shown) connected to the port 51 is led out from the opening 11 of the pressure bag 1.

In a state in which the bag-shaped container 50 is housed in the housing chamber 10, air is supplied to the pressure chamber 15 of the pressure bag 1 via the communicating tube 17. The pressure chamber 15 is inflated with the supplied air. As the pressure chamber 15 is inflated, the bag-shaped container 50 adjacent to the pressure chamber 15 is compressed. The pressure chamber 15 is pressurized to a predetermined pressure (e.g., 40 kPa). After that, the clamp on the extension tube is opened. The liquid substance is squeezed out through the port 51. After the squeezing of the liquid substance out of the bag-shaped container 50 is completed, the pressure in the pressure chamber 15 is released. The flattened bag-shaped container 50 is taken out of the housing chamber 10.

The use of the pressure bag 1 of the present invention makes it possible to almost squeeze out all of the liquid substance in the bag-shaped container 50. This will be described below.

In the squeezing device of Patent Document 1 above, a pressure bag is disposed on only one side of the bag-shaped container. In the squeezing device of Patent Document 2, pressure bags are disposed on both sides of the bag-shaped container. In both of these squeezing devices, when a pressure bag is inflated, a surface of the pressure bag that faces the bag-shaped container bulges into a dome-like shape. Thus, the pressure bag depresses a substantially middle portion of a side surface of the bag-shaped container the most. If the substantially middle portion of the bag-shaped container is flattened first, it is difficult for the liquid substance that is present on the opposite side (hereinafter referred to as "non-port side") of the substantially middle portion from the port to flow toward the port side. As a result, in the conventional squeezing devices, the liquid substance remains on the non-port side, and it is difficult to squeeze out all of the liquid substance in the bag-shaped container.

Figure 4:
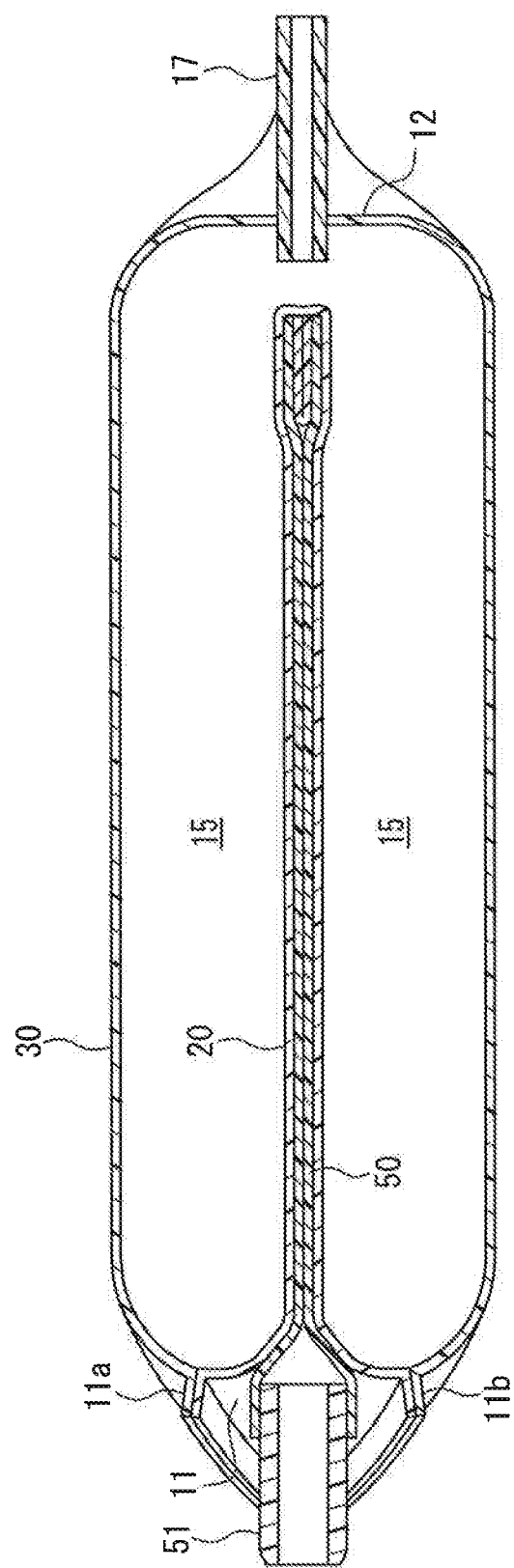
FIG. 4 is a cross-sectional view showing a state in which a liquid substance in the bag-shaped container has been squeezed out of the bag-shaped container with use of the pressure bag according to Embodiment 1 of the present invention.

FIG. 4 is a cross-sectional view showing a state in which the pressure bag 1 with the pressure chamber 15 inflated applies pressure to the bag-shaped container 50. In FIG. 4, the tube connected to the communicating tube 17 and the extension tube connected to the port 51 are not shown. In the pressure bag 1 of the present invention, the inner sheet 20 that is folded back constitutes the inner surface of the housing chamber 10 in which the bag-shaped container 50 is housed, and the pressure chamber 15 extends along this inner sheet 20, from one side to the other side of the bag-shaped container 50 via the bottom portion 12. For this reason, when the pressure chamber 15 is inflated, the inner sheet 20 also comes into contact with and applies pressure to a portion of the bag-shaped container 50 that is located on the non-port side, as is the case with the other portions of the bag-shaped container 50. A nonuniform pressure distribution in which the pressure applied to the bag-shaped container 50 is at its maximum in the middle portion of the bag-shaped container 50 in the long-side direction and lowers on opposite sides of the middle portion and which may be created by a conventional squeezing device is no longer created by the pressure bag 1 of the present invention. As a result, when the pressure bag 1 is used, the liquid substance is prevented from remaining on the non-port side, and the amount of liquid substance remaining in the bag-shaped container 50 after being squeezed out of the bag-shaped container 50 can be reduced.

Moreover, the pressure bag 1 of the present invention has an extremely simple structure, compared with the squeezing device of Patent Document 2, in which pressure bags are disposed on both sides of the bag-shaped container. Also, as can be readily understood from the above-described production method, the pressure bag 1 of the present invention can be produced in an extremely easy manner, in which the two sheets 20 and 30 are folded back (i.e., folded in half) and bonded to each other.

The communicating tube 17 being provided in the folding-back portion 31 of the outer sheet 30 makes it possible to reduce the thickness of the pressure bag 1 when not in use, and is therefore advantageous in making it easy to store the pressure bag 1.

Embodiment 2

Figure 5:
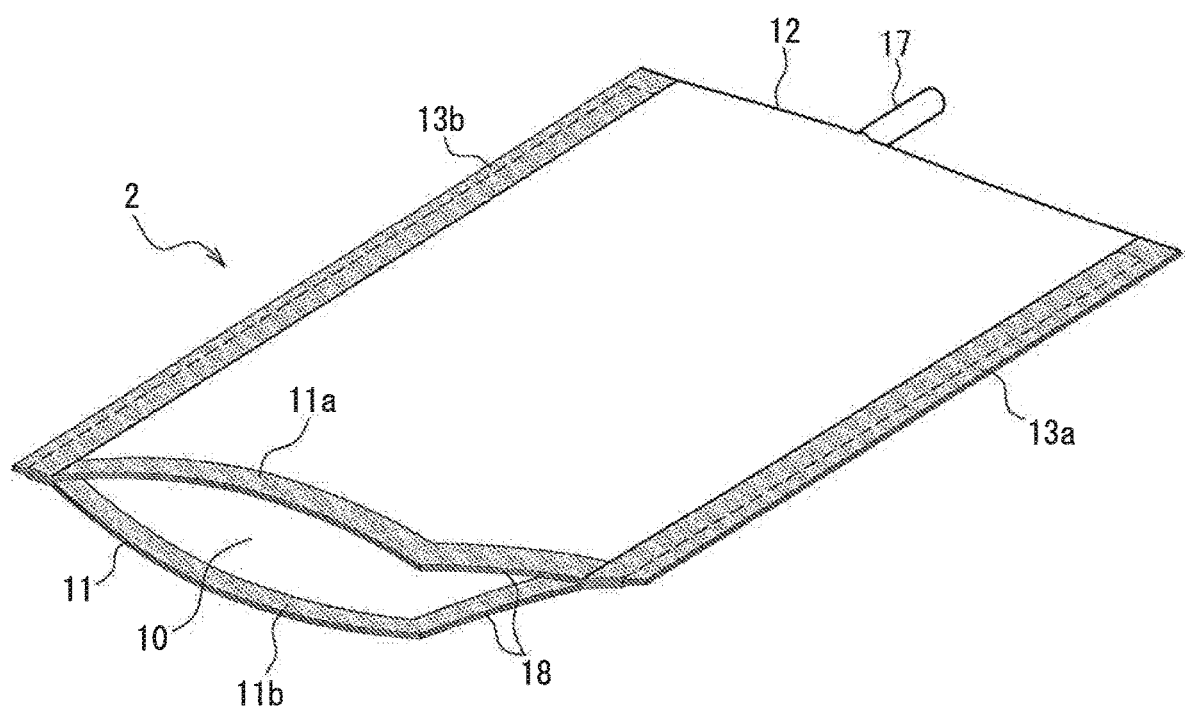
FIG. 5 is a perspective view of a pressure bag according to Embodiment 2 of the present invention.

FIG. 5 is a perspective view of a pressure bag 2 according to Embodiment 2 of the present invention. Embodiment 2 will be described focusing primarily on the differences from Embodiment 1.

The above-described pressure bag 1 of Embodiment 1 has a substantially rectangular shape in a plan view. In contrast, the pressure bag 2 of Embodiment 2 has a substantially pentagonal shape in a plan view. An oblique end edge 18 is provided in the pressure bag 2 by cutting off one of the corners of the short side on which the opening 11 is provided. As described above, a bag-shaped container in which a port is provided inclined in a corner portion where a short side and a long side intersect each other actually exists. The pressure bag 2 can be favorably used for such a bag-shaped container. If the bag-shaped container is housed in the housing chamber 10 such that the inclined port is located in a portion of the oblique end edge 18, the likelihood that the port will collide with the pressure bag 2 can be reduced. This is advantageous in reducing the amount of liquid substance remaining near the port after the liquid substance is squeezed out.

Embodiment 2 is the same as Embodiment 1 except for the above-described points. Descriptions of Embodiment 1 also apply to Embodiment 2.

Embodiment 3

Figure 6A:
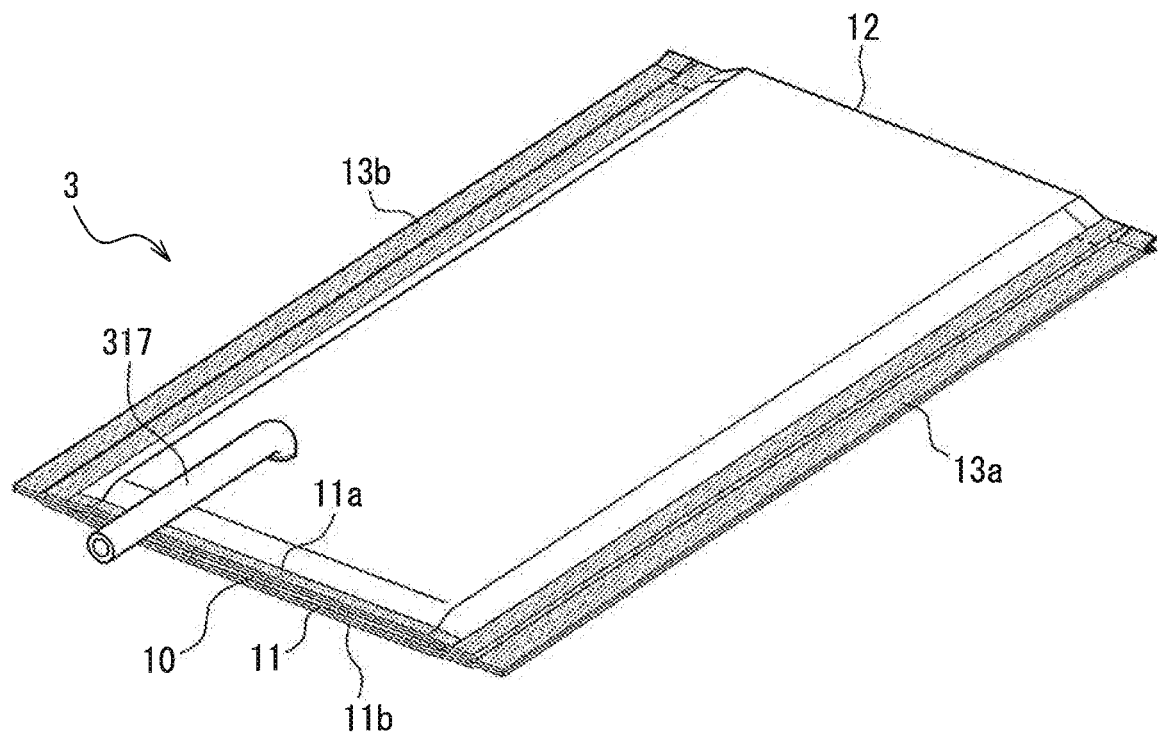
FIG. 6A is a perspective view of a pressure bag according to Embodiment 3 of the present invention when viewed from an opening side.
Figure 6B:
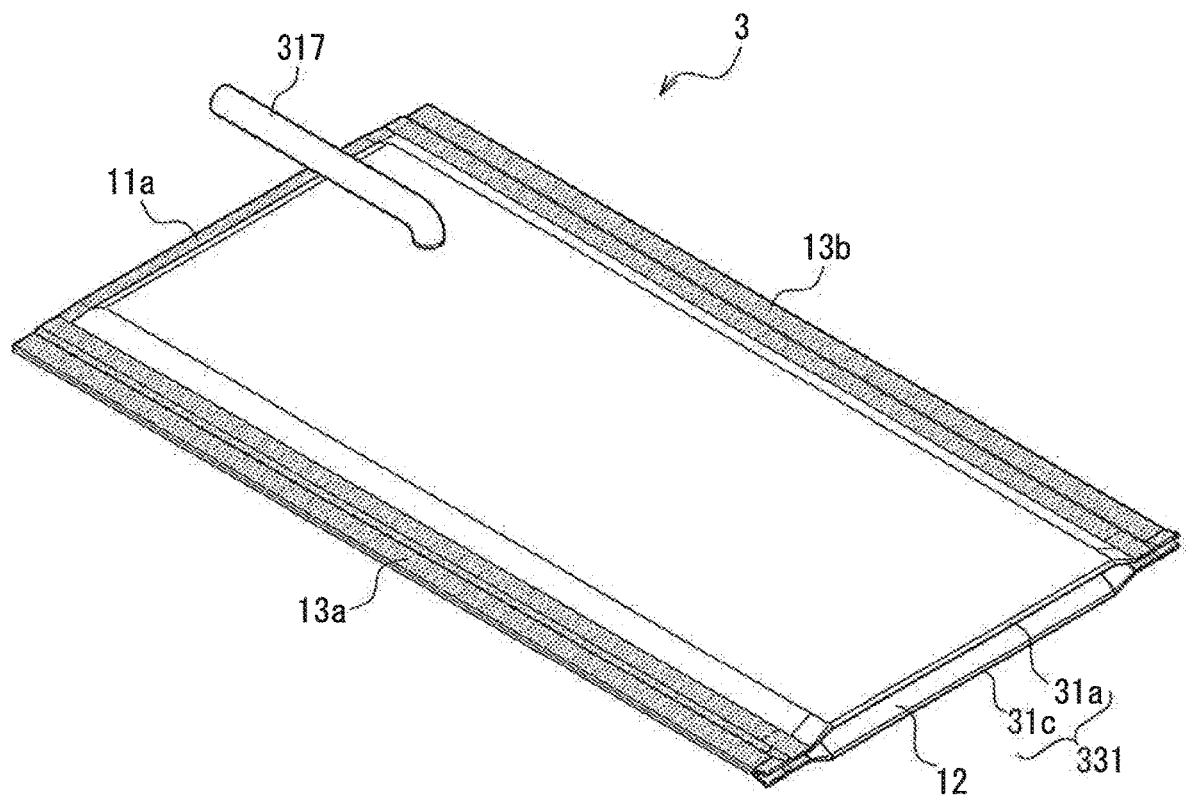
FIG. 6B is a perspective view of the pressure bag according to Embodiment 3 of the present invention when viewed from a bottom portion side.
Figure 6C:
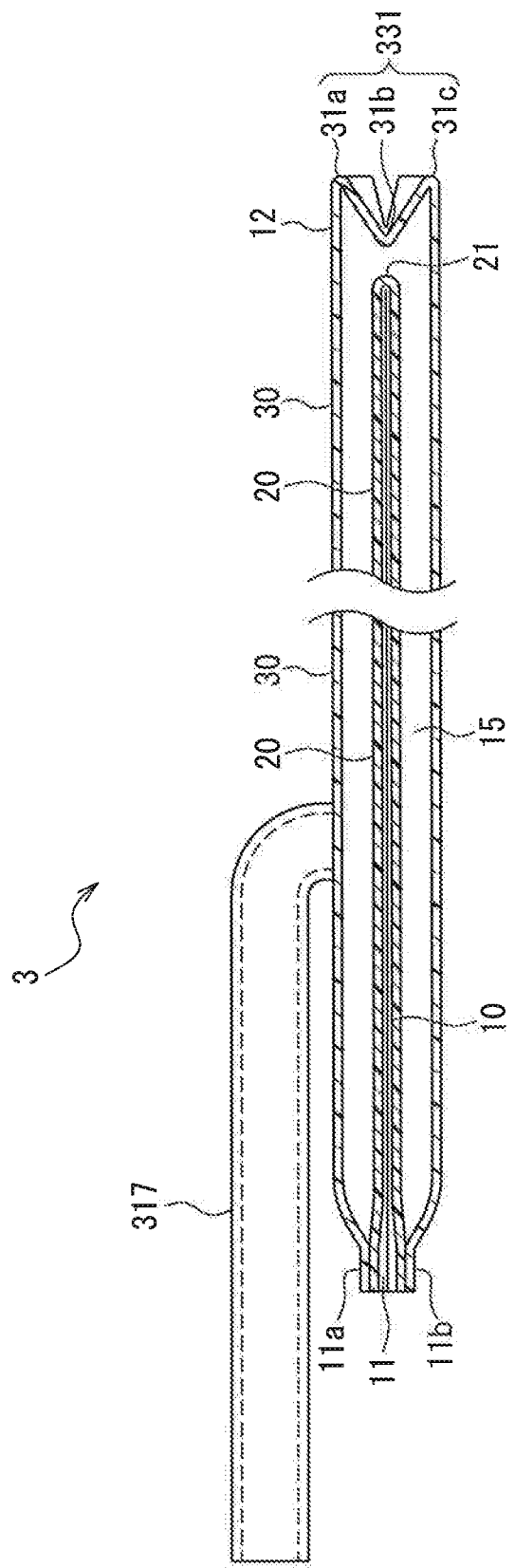
FIG. 6C is a cross-sectional view of the pressure bag according to Embodiment 3 of the present invention.

FIG. 6A is a perspective view of a pressure bag 3 according to Embodiment 3 of the present invention when viewed from the opening 11 side, and FIG. 6B is a perspective view of the pressure bag 3 when viewed from the bottom portion 12 side. FIG. 6C is a cross-sectional view of the pressure bag 3 taken along a plane that is parallel to the insertion and withdrawal direction. In FIG. 6C, the opening 11 and portions near the opening 11, as well as the bottom portion 12 and portions near the bottom portion 12 are shown in an enlarged manner, and portions located therebetween are not shown. Embodiment 3 will be described focusing primarily on the differences from Embodiment 1.

As is best shown in FIG. 6C, the outer sheet 30 is folded at three folds 31a, 31b, and 31c into a substantially "M" shape. More specifically, when viewed from the outside of the pressure bag 3, the outer sheet 30 is mountain-folded at the folds 31a and 31c and valley-folded at the fold 31b between the folds 31a and 31c. The three folds 31a, 31b, and 31c constitute a folding-back portion 331 of the outer sheet 30. The folding-back portion 331 can be formed by folding the outer sheet 30 in alternately opposite directions at the three folds 31a, 31b, and 31c, instead of the fold 31' (see FIG. 3B) of Embodiment 1. The configuration in which the folding-back portion 21 of the inner sheet 20 and the folding-back portion 331 of the outer sheet 30 are spaced apart from each other in the insertion and withdrawal direction (left-right direction in FIG. 6C) is the same as that of Embodiment 1. As a result of the outer sheet 30 being folded into an accordion-like shape (or bellows-like shape) in the folding-back portion 331, when the pressure chamber 15 is inflated, the folding-back portion 331 of the outer sheet 30 largely bulges outward. This reduces the likelihood that the inner sheet 20 and the outer sheet 30 will come into contact with each other at the bottom portion 12, and is therefore advantageous in securing the communication of the pressure chamber 15 at the bottom portion 12. The number, the spacing, and the like of folds that constitute the folding-back portion 331 are not limited to those of Embodiment 3 and may be changed as desired.

A communicating tube 317 corresponds to the communicating tube 17 of Embodiment 1. As shown in FIGS. 6A to 6C, the communicating tube 317 is bent into a substantially "L" shape, and is provided in a region of the outer sheet 30 between the opening 11 and the folding-back portion 331 (or the bottom portion 12). As is the case with Embodiment 1, the portion of the pressure chamber 15 that is located on one side of the housing chamber 10 and the portion of the pressure chamber 15 that is located on the other side of the housing chamber 10 are in communication with each other via the bottom portion 12, and therefore, even when the communicating tube 317 is provided on one side, it is possible to inflate the entire pressure chamber 15.

A leading end of the communicating tube 317 is located near the opening 11 of the pressure bag 3 and is open toward the same side as the opening 11. For this reason, a tube that is connected to the communicating tube 317 extends toward the same side as the extension tube that is connected to the port 51 (see FIG. 1) of the bag-shaped container 50 that is housed in the housing chamber 10. This is advantageous in improving the ease of handling of these two tubes and the ease of the operation of squeezing the liquid substance out of the bag-shaped container 50.

Embodiment 3 is the same as Embodiment 1 except for the above-described points. Descriptions of Embodiment 1 also apply to Embodiment 3. The folding-back portion 331 and/or the communicating tube 317 of Embodiment 3 may also be applied to Embodiments 1 and 2.

In Embodiment 3, the folding-back portion 21 (see FIG. 6C) of the inner sheet 20 may also be constituted by a plurality of folds, as is the case with the folding-back portion 331 of the outer sheet 30. This configuration may also be applied to Embodiments 1 and 2, as well as Embodiment 4, which will be described later.

Embodiment 4

Figure 7A:
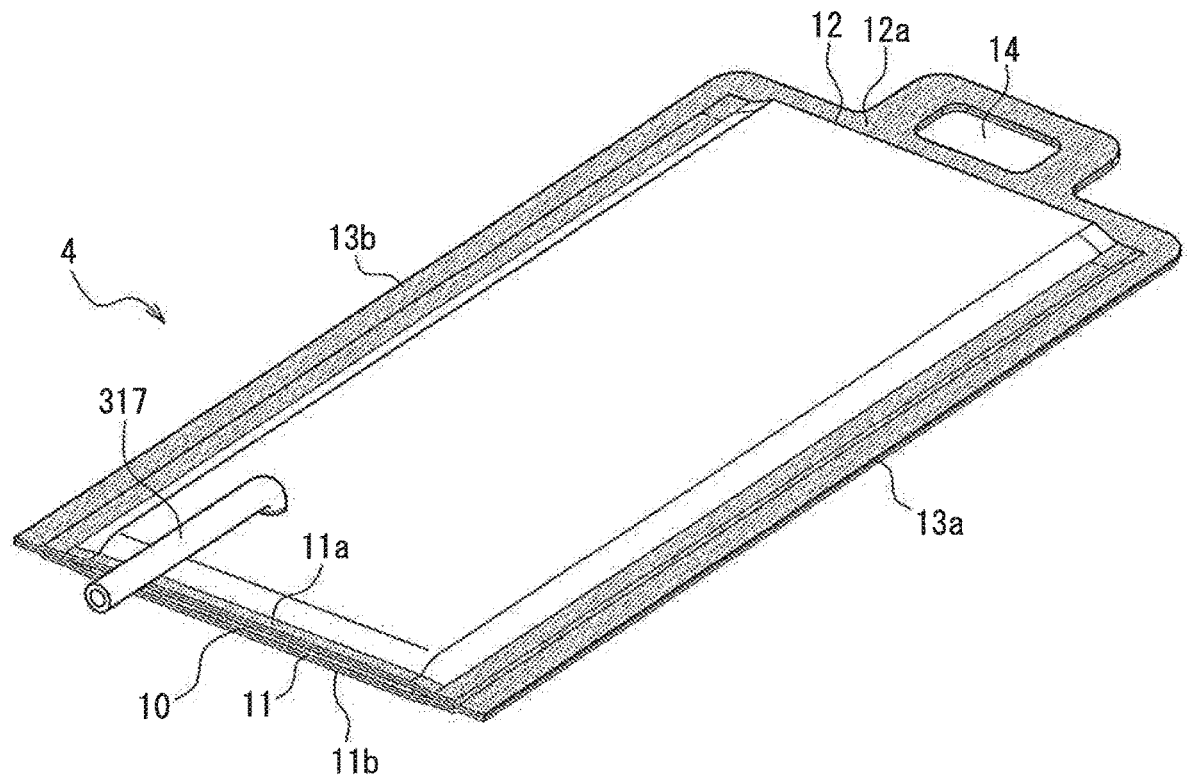
FIG. 7A is a perspective view of a pressure bag according to Embodiment 4 of the present invention when viewed from an opening side.
Figure 7B:
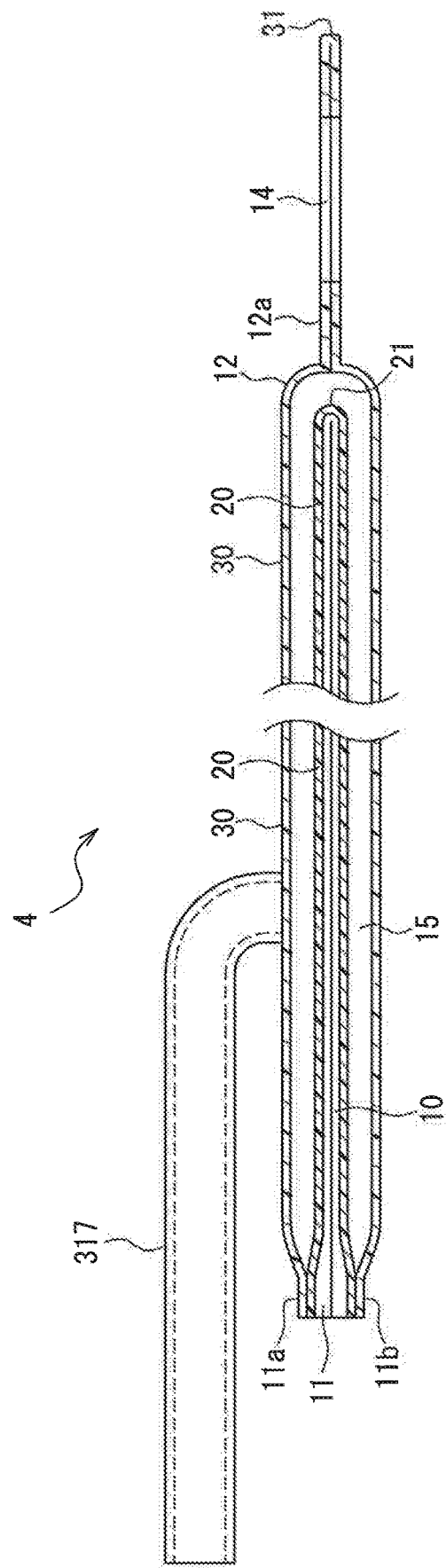
FIG. 7B is a cross-sectional view of the pressure bag according to Embodiment 4 of the present invention.

FIG. 7A is a perspective view of a pressure bag 4 according to Embodiment 4 of the present invention when viewed from the opening 11 side. FIG. 7B is a cross-sectional view of the pressure bag 4 taken along a plane that is parallel to the insertion and withdrawal direction. FIG. 7B shows the opening 11 and portions near the opening 11, as well as the bottom portion 12 and portions near the bottom portion 12, in an enlarged manner, and portions therebetween are not shown. Embodiment 4 will be described focusing primarily on the differences from Embodiment 1.

As shown in FIG. 7A, a bottom seal portion 12a is provided along a short side on the bottom portion 12 side. The bottom seal portion 12a is continuous with the lateral side seal portions 13a and 13b. Both end portions of an outer peripheral end edge of the bottom seal portion 12a are cut away, and only a middle portion of the bottom seal portion 12a protrudes outward. A through hole 14 passing through the bottom seal portion 12a is provided in the protruding middle portion of the bottom seal portion 12a. In FIG. 7A, the bottom seal portion 12a is shaded with numerous dots like the seal portions 11a, 11b, 13a, and 13b.

As shown in FIG. 7B, in the bottom seal portion 12a, the two layers of the outer sheet 30, which is folded back at the folding-back portion 31, are laminated and joined together. This bottom seal portion 12a can be formed by forming, in Embodiment 1, a sealant region (a region to which a sealant is applied) with a constant width along the fold 31' (see FIG. 3B) so as to connect the pair of sealant regions 33b, and joining the sealant region at the same time as joining the sealant regions 23b and 33b together.

The through hole 14 can be used in suspending the pressure bag 4 from a hook or the like. Since the through hole 14 is provided in the bottom seal portion 12a, where the two layers of the outer sheet 30 are laminated and joined together, an end edge surrounding the through hole 14 has high strength.

In a state in which the bag-shaped container 50 is housed in the housing chamber 10, the pressure bag 4 may be suspended with the through hole 14 located on the upper side. The liquid substance in the bag-shaped container 50 flows down toward the port 51 (see FIG. 1) due to gravity, and therefore, the amount of liquid substance remaining in the bag-shaped container 50 after squeezing out can be reduced even further. A detachment preventing structure that prevents the bag-shaped container 50 from coming out of the pressure bag 4 may also be provided in the pressure bag 4. The detachment preventing structure may be, but is not limited to, for example, a band spanning between the opening seal portion 11a and the opening seal portion 11b or a fastener that connects the opening seal portion 11a and the opening seal portion 11b to each other.

In Embodiment 4, it is also possible to cut off the folding-back portion 31 (see FIG. 7B) of the outer sheet 30 at the same time as cutting both end portions of the bottom seal portion 12a away. Alternatively, both end portions of the bottom seal portion 12a may not be cut away. A plurality of through holes 14 may also be provided in the bottom seal portion 12a.

The communicating tube 317 is the same as the communicating tube 317 of Embodiment 3. When the pressure bag 4 is suspended with the through hole 14 located on the upper side in a state in which the bag-shaped container 50 is housed in the housing chamber 10 as described above, both the leading end of the communicating tube 317 and the port 51 (see FIG. 1) of the bag-shaped container 50 face downward. Both the tube connected to the communicating tube 317 and the extension tube connected to the port 51 hang down due to gravity. This prevents these two tubes from being bent and blocked, and therefore, the ease of the operation of squeezing the liquid substance out of the bag-shaped container 50 is favorable.

Embodiment 4 is the same as Embodiment 1 except for the above-described points. Descriptions of Embodiment 1 also apply to Embodiment 4. The bottom seal portion 12a and the through hole 14 of Embodiment 4 may also be applied to Embodiments 1 to 3.

Embodiment 5

Figure 8:
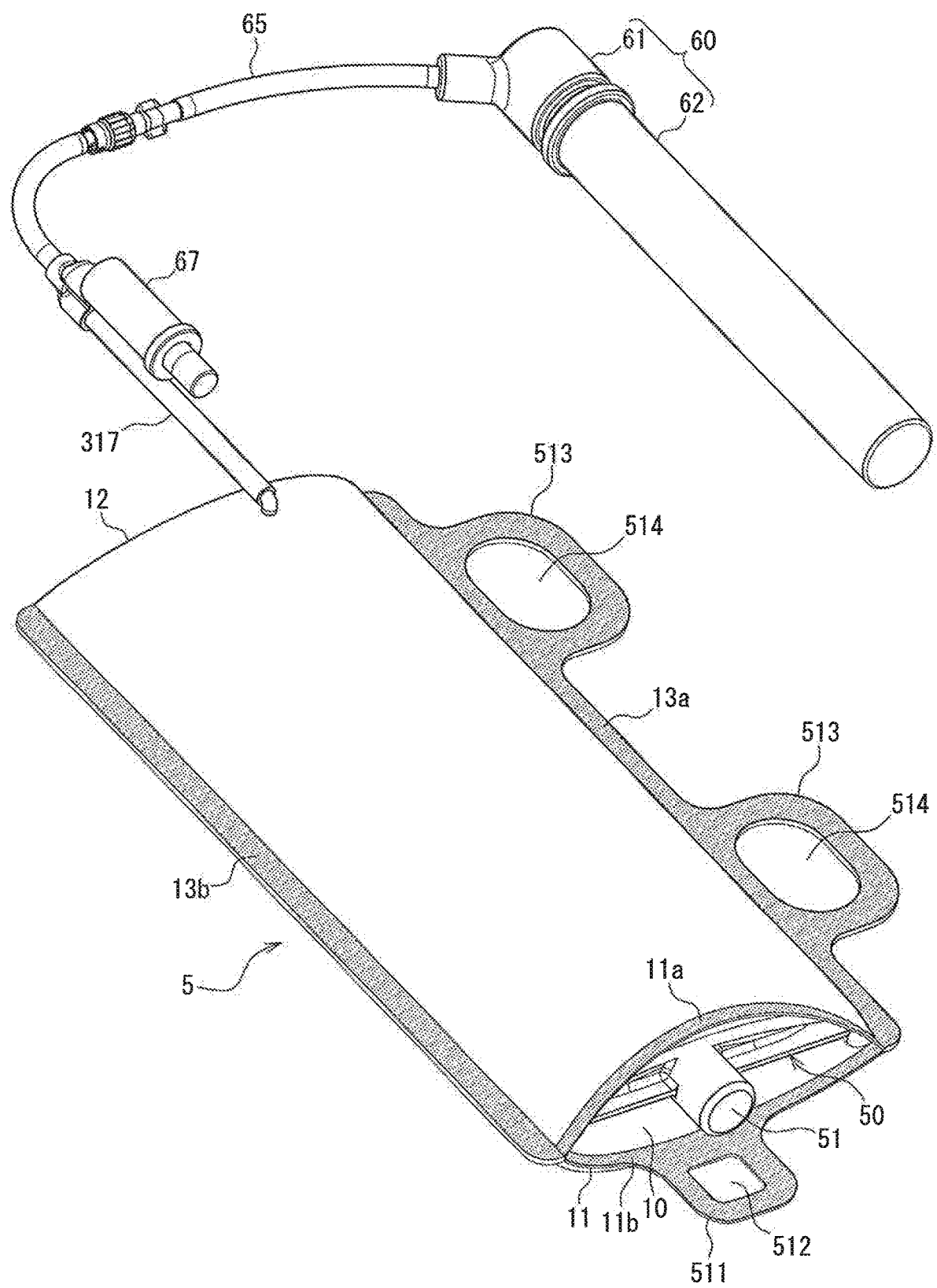
FIG. 8 is a perspective view showing a pressure bag according to Embodiment 5 of the present invention, with a bag-shaped container housed therein.

FIG. 8 is a perspective view of a pressure bag 5 according to Embodiment 5 of the present invention. The bag-shaped container 50 is housed in the housing chamber 10 of the pressure bag 5. A connecting tube 317 is provided near the bottom portion 12 of the pressure bag 5. A manual piston pump 60 is connected to the connecting tube 317 via a pliable tube 65. The piston pump 60 is capable of feeding air as a result of a handle 62 being moved back and forth in a longitudinal direction thereof relative to a base portion 61. A pressure gauge 67 is provided on a connector that connects the tube 65 to the connecting tube 317. The pressure gauge 67 displays the pressure in the pressure chamber of the pressure bag 5. The pressure gauge 67 has a limiter function of releasing air in the pressure chamber to the outside if the pressure in the pressure chamber exceeds a predetermined value and thereby keeping the pressure in the pressure chamber at the predetermined value or less. A pressure release valve (e.g. three-way stopcock, which is not shown) for manually releasing air to the outside may also be provided on the tube 65.

The pressure bag 5 includes an engagement projection 511 at an end edge of the opening 11, and also includes two through holes 514 in the lateral side seal portion 13a.

The engagement projection 511 is formed by a substantially middle portion of the opening seal portion 11b locally protruding outward. A through hole 512 passing through the engagement projection 511 is formed in the engagement projection 511. As a result, the engagement projection 511 protrudes from the opening seal portion 11b in a substantially "U" shape as a whole. In FIG. 8, the engagement projection 511 is curved upward (toward the opening seal portion 11a side), and the port 51 of the bag-shaped container 50 is inserted into the through hole 512. After that, an extension tube (e.g., enteral nutrition set, which is not shown) is connected to the port 51. The engagement projection 511 that is engaged with the port 51 holds the bag-shaped container 50 so that the bag-shaped container 50 is prevented from coming out of the pressure bag 5. For example, when inflating the pressure bag 5 by using the piston pump 60, it is possible to prevent the bag-shaped container 50 from coming out of the pressure bag 5 due to the pressure bag 5 being gradually inflated.

The engagement projection 511 may also be formed by the entire opening seal portion 11b in the longitudinal direction thereof, instead of only a portion of the opening seal portion 11b in the longitudinal direction thereof, protruding further than the opening seal portion 11a. The engagement projection 511 may also be provided in the opening seal portion 11a.

The through holes 514 are provided in respective protruding portions 513 formed by the lateral side seal portion 13a locally protruding outward. The through holes 514 can be used in the following manner. In a state in which the bag-shaped container 50 is housed in the pressure bag 5 as shown in FIG. 8, the pressure chamber of the pressure bag 5 is pressurized to a predetermined pressure by using the piston pump 60. After that, the piston pump 60 that has a rod-like shape is inserted into the two through holes 514. For example, the piston pump 60 is inserted into one of the through holes 514 from above, and then inserted into the other through hole 514 from below. The piston pump 60 is held by the pressure bag 5. In this state, a clamp provided on the extension tube connected to the port 51 is opened, thereby causing the liquid substance to start flowing out of the bag-shaped container 50.

The pressure bag 5 pressurized to the predetermined pressure inflates into a substantially cylindrical shape as a whole, with an axial direction thereof coinciding with the insertion and withdrawal direction in which the bag-shaped container 50 is inserted into and withdrawn from the housing chamber 10. A period of time elapses from start to finish of the liquid substance flowing out of the bag-shaped container 50. During that period, the pressure bag 5 remains inflated in the substantially cylindrical shape. In a state in which the piston pump 60 is not inserted into the through holes 514, the substantially cylindrical pressure bag 5 is likely to roll. For example, in the case where enteral nutrition therapy is performed, even if the pressure bag 5 is placed on the bed of a patient, the pressure bag 5 may be likely to roll and fall from the bed. When the piston pump 60 is attached to the pressure bag 5 by inserting the piston pump 60 into the through holes 514, the weight of the piston pump 60 can prevent the pressure bag 5 from rolling.

Instead of providing the protruding portions 513 by making the lateral side seal portion 13a locally protrude outward, it is also possible to increase the width of the lateral side seal portion 13a over the entire length in the longitudinal direction thereof and provide the through holes 514 in the widened lateral side seal portion 13a.

The number of through holes 514 need not be two, and may be one or three or more. The through holes 514 can be provided in any one of, or both of, the lateral side seal portions 13a and 13b. The through holes 514 may also be provided on the bottom portion 12 side. For example, as is the case with the through hole 14 of Embodiment 4, a through hole 514 into which the piston pump 60 can be inserted may be provided in the bottom seal portion 12a.

In the pressure bag 5, either the engagement projection 511 or the through holes 514 may be omitted as desired.

Embodiment 5 is the same as Embodiment 1 except for the above-described points. Descriptions of Embodiment 1 also apply to Embodiment 5. Either of or both the engagement projection 511 and the through holes 514 of Embodiment 5 may also be applied to Embodiments 1 to 4.

Embodiment 6

Figure 9:
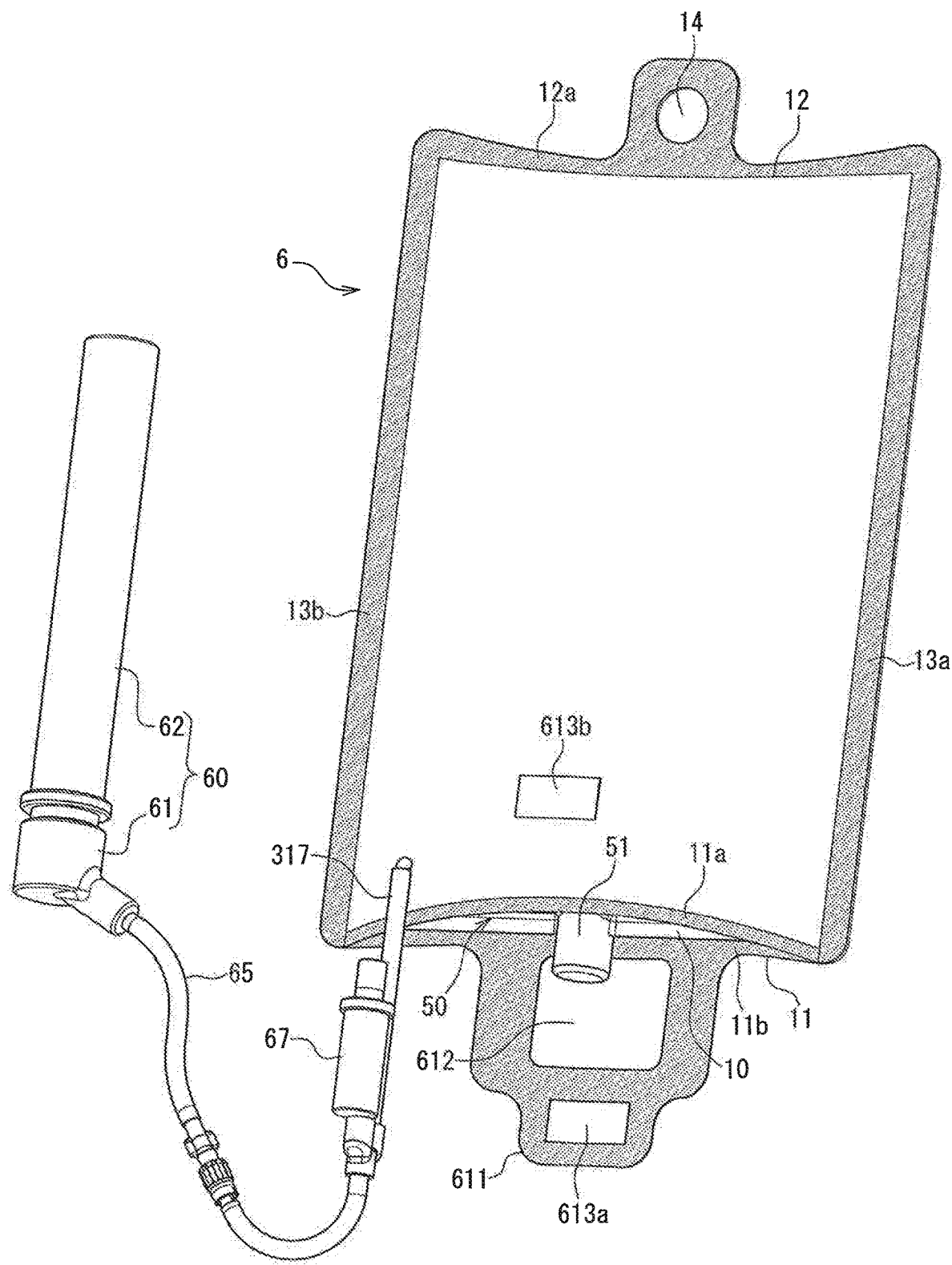
FIG. 9 is a perspective view showing a pressure bag according to Embodiment 6 of the present invention, with a bag-shaped container housed therein.

FIG. 9 is a perspective view of a pressure bag 6 according to Embodiment 6 of the present invention. The bag-shaped container 50 is housed in the housing chamber 10 of the pressure bag 6. The pressure bag 6 includes an engagement projection 611 at an end edge of the opening 11 thereof. Furthermore, as is the case with Embodiment 4, the pressure bag 6 includes the bottom seal portion 12a in which the through hole 14 is provided.

The engagement projection 611 is formed by a substantially middle portion of the opening seal portion 11b locally protruding outward. A through hole 612 passing through the engagement projection 611 is formed in the engagement projection 611. The engagement projection 611 is provided with a hook-and-loop fastener 613a at a position that is closer to a leading end of the engagement projection 611 than the through hole 612. A hook-and-loop fastener 613b is provided at a position on the outer surface of the pressure bag 6 that is located close to the opening seal portion 11a. The hook-and-loop fastener 613a and the hook-and-loop fastener 613b constitute fixing means that can be repeatedly attached to and detached from each other (opened and closed), and an example thereof is Magic Tape (registered trademark). In FIG. 9, the engagement projection 611 is curved upward (toward the opening seal portion 11a side), and the port 51 of the bag-shaped container 50 is inserted into the through hole 612. The hook-and-loop fastener 613a is fixed to the hook-and-loop fastener 613b. After that, an extension tube (e.g., enteral nutrition set, which is not shown) is connected to the port 51. The pressure bag 6 is suspended on a hook with the through hole 14, with the opening 11 located on the lower side. Since the hook-and-loop fastener 613a and the hook-and-loop fastener 613b are fastened to each other, the bag-shaped container 50 is prevented from coming out of the pressure bag 6.

The engagement projection 611 is not limited to a projection that is formed by only a portion of the opening seal portion 11b in the longitudinal direction thereof protruding outward, but may also be formed by the entire opening seal portion 11b in the longitudinal direction thereof protruding further than the opening seal portion 11a. The engagement projection 611 may also be provided in the opening seal portion 11a. The engagement projection 611 may merely be an elongated band (strip-shaped member) that has no through hole 612, and in this case as well, it is possible to prevent the bag-shaped container 50 from coming out of the pressure bag 6.

An attachment and detachment mechanism for attaching and detaching the leading end of the engagement projection 611 to and from the outer surface of the pressure bag 6 is not limited to the hook-and-loop fasteners 613a and 613b, and may be any mechanism (e.g., a snap button, a button, and the like) other than the hook-and-loop fasteners 613a and 613b. It is also possible to omit the hook-and-loop fasteners 613a and 613b. As is the case with Embodiment 5, it is possible to prevent the bag-shaped container 50 from coming out of the pressure bag 6 even by simply inserting the port 51 into the through hole 612 and thereby engaging the engagement projection 611 with the port 51.

Embodiment 6 is the same as Embodiment 1 except for the above-described points. Descriptions of Embodiment 1 also apply to Embodiment 6. Either of or both the engagement projection 611 and the through hole 14 of Embodiment 6 may also be applied to Embodiments 1 to 5.

It should be understood that Embodiments 1 to 6 are given by way of example only. The present invention is not limited to Embodiments 1 to 6 above, and modifications can be made thereto as appropriate.

In Embodiments 1 to 6 above, the outer sheet 30 is larger than the inner sheet 20 both in the long-side direction and in the short-side direction, but the present invention is not limited to this.

For example, in Embodiments 1 and 2, the outer sheet 30 may have the same size as the inner sheet 20 in the long-side direction. In this case, unlike Embodiments 1 and 2 above, the folding-back portion 21 of the inner sheet 20 that is folded back and the folding-back portion 31 of the outer sheet 30 that is folded back are in contact with each other in the insertion and withdrawal direction. However, in this case as well, the pressure chamber 15 can extend from one side to the other side of the housing chamber 10 via the bottom portion 12, and therefore, similar effects as those of Embodiments 1 and 2 above can be obtained. Moreover, when the pair of short sides of the inner sheet 20 are joined to the pair of short sides of the outer sheet 30, unlike Embodiment 1 above, the middle portion of the outer sheet 30 does not generate slack (see FIG. 3B), and therefore, in the production process of the pressure bag 1, it is easy to handle the inner sheet 20 and the outer sheet 30 that are joined together in this manner.

Moreover, the outer sheet 30 may also have the same size as the inner sheet 20 in the short-side direction. In this case, it is preferable to provide sealant regions extending along the long sides of the inner sheet 20 on a surface (upper surface of the inner sheet 20 in FIG. 3A) of the inner sheet 20 that is located on the opposite side to the outer sheet 30.

The outer sheet 30 may also be composed of two outer sheet pieces that are separated from each other at a position corresponding to the folding-back portion 31. In this case, the two outer sheet pieces are joined to each other at the bottom portion 12. Portions of the two outer sheet pieces that are joined to each other can constitute a seal portion similar to the bottom seal portion 12a of Embodiment 4. Similarly, the inner sheet 20 may also be composed of two inner sheet pieces that are separated from each other at a position corresponding to the folding-back portion 21.

The pressure bags 1 to 6 of Embodiments 1 to 6 above are produced using the inner sheet 20 and the outer sheet 30 (see FIG. 3A) that are independent of each other, but the present invention is not limited to this. For example, a pressure bag of the present invention can be composed using a single continuous sheet in which one of the short sides of the inner sheet 20 and one of the short sides of the outer sheet 30 are connected to each other. In this case, the single sheet is folded at the boundary between the inner sheet and the outer sheet. Then, both ends of the single sheet are laid one on top the other and joined together. After that, the pressure bag can be produced in a manner similar to that of the foregoing embodiments (see FIGS. 3B and 3C). In the thus produced pressure bag, one of the opening seal portions 11a and 11b (see FIG. 1) of the pressure bags 1 to 6 of the foregoing embodiments is changed to the folding-back portion along the boundary between the inner sheet and the outer sheet.

In Embodiments 1 to 6 above, portions of the inner sheet 20 other than the outer peripheral end edges thereof are not joined to the outer sheet 30. However, as long as the communication of the pressure chamber 15 via the bottom portion 12 is secured, for example, the folding-back portion 21 of the inner sheet 20 and the folding-back portion 31 of the outer sheet 30 may be partially joined to each other. This may be advantageous in preventing a portion of the folding-back portion 21 of the inner sheet 20 from being deformed such that the portion is pushed into the housing chamber 10 when the pressure chamber 15 is inflated.

In Embodiments 1 to 6 above, the inner sheet 20 and the outer sheet 30 are joined to each other using a heat sealing method, but as long as the two sheets can be joined to each other in an airtight (or liquid-tight) manner, the method for joining the two sheets 20 and 30 to each other is not limited to heat sealing. For example, the two sheets can be joined to each other using a method in which an adhesive or pressure-sensitive adhesive tape (double-sided pressure-sensitive adhesive tape or single-sided pressure-sensitive adhesive tape) is used, a fusion-bonding method, a method in which the two sheets are sewed together with a thread, a combination of these methods, or the like.

The position at which the communicating tube is provided is not limited to those described in the foregoing embodiments. For example, the communicating tube may be provided at any position on the outer sheet 30, or may be provided in an opening seal portion (11a or 11b) or a lateral side seal portion (13a or 13b) in a state in which the communicating tube is sandwiched between the inner sheet 20 and the outer sheet 30. The shape of the communicating tube is not limited to a straight line shape or an L shape, and may be any shape. A plurality of communicating tubes may also be provided in the pressure bag.

The position of the through hole 14 is not limited to the bottom seal portion 12a (see FIGS. 7A and 9). For example, the through hole 14 may also be provided in the lateral side seal portion 13a or 13b. In this case, it is possible to omit the bottom seal portion 12a.

INDUSTRIAL APPLICABILITY

Although there is no limitation on the field of application of the present invention, the present invention can be favorably used for pressure bags for squeezing a liquid substance (in particular, semi-solid low-fluidity fluid substance) contained in a bag-shaped container out of the bag-shaped container. The present invention can be favorably used in the medical field, in particular, for enteral nutrition therapy in which a semi-solid nutritional agent is injected into a patient via a catheter inserted into the body of the patient. However, the present invention is not limited to the medical field, and can also be extensively used in various fields (e.g., the fields of food, general industry, and the like) in which it is necessary to inject a liquid substance.

DESCRIPTION OF REFERENCE NUMERALS 1, 2, 3, 4, 5, 6 Pressure bag
10 Housing chamber
11 Opening
12 Bottom portion
15 Pressure chamber
17, 317 Communicating tube
20 Inner sheet
21 Folding-back portion of inner sheet
30 Outer sheet
31 Folding-back portion of outer sheet
50 Bag-shaped container

The invention claimed is:

1. A pressure bag comprising:
a housing chamber configured to house a bag-shaped container in which a liquid substance is contained; and
a hermetically-sealed pressure chamber,
the pressure bag having, at one end, an opening through which the bag-shaped container is placed into and taken out of the housing chamber, having a bottom portion on an opposite side to the opening, and having first and second lateral side seal portions along first and second lateral sides of the pressure bag that connect the opening and the bottom portion to each other,
the pressure bag comprising a folded, flexible inner sheet formed of a single continuous sheet, and a folded, flexible outer sheet formed of a single continuous sheet located on an opposite side of the inner sheet from the housing chamber, the flexible inner sheet and the flexible outer sheet having folding-back portions that are disposed at a bottom portion side of the pressure bag that is opposite the opening of the pressure bag,
wherein the flexible outer sheet is longer than the flexible inner sheet in a direction in which the first and second lateral side seal portions face each other, and the flexible inner sheet has a first surface that faces the housing chamber and a second surface that faces the flexible outer sheet, with outer peripheral edges of the second surface of the flexible inner sheet being entirely joined to the outer sheet, and the opening extending between facing portions of the first surface of the flexible inner sheet,
each of the first and second lateral side seal portions has a first zone in which the flexible inner sheet is present and a second zone in which the flexible inner sheet is not present, with the second zone present at a peripheral edge side of the first zone,
in the first zones of each of the first and second lateral side seal portions, a respective lateral side of the flexible inner sheet is joined to a respective lateral side of the flexible outer sheet, with the first surface of the lateral side of the flexible inner sheet not joined to itself,
in the second zones of each of the first and second lateral side seal portions, the respective lateral side of the flexible outer sheet is joined to itself without intervening flexible inner sheet,
the pressure chamber is present between the flexible inner sheet and the flexible outer sheet,
each of the flexible inner sheet, the flexible outer sheet, and the pressure chamber extends continuously from a first side of the housing chamber to a second side of the housing chamber via the bottom portion, and
the pressure bag is configured such that, when a fluid is injected into the pressure chamber, the pressure chamber is inflated and applies pressure to a bag-shaped container housed in the housing chamber so as to squeeze liquid substance out of the bag-shaped container.

2. The pressure bag according to claim 1, wherein, at the bottom portion, the inner sheet and the outer sheet are spaced apart from each other in a direction in which the bag-shaped container is placed into and taken out of the housing chamber.

3. The pressure bag according to claim 1, wherein, at the bottom portion, the inner sheet and the outer sheet are not joined to each other.

4. The pressure bag according to claim 1, wherein the inner sheet constitutes a surface of the housing chamber, and the outer sheet constitutes an outer surface of the pressure bag.

5. The pressure bag according to claim 1, further comprising a communicating tube through which the fluid is injected into the pressure chamber.

6. The pressure bag according to claim 1, further comprising a heat sealant material that joins the second surface of the flexible inner sheet to the flexible outer sheet around the periphery of the flexible inner sheet, and that joins facing portions of the respective lateral side of the flexible outer sheet in the second zones of each of the first and second lateral side seal portions.

* * * * *